United States Patent [19]

Sun et al.

[11] Patent Number: 4,772,459
[45] Date of Patent: Sep. 20, 1988

[54] METHOD FOR CONTROLLING EMESIS CAUSED BY CHEMOTHERAPEUTIC AGENTS AND ANTIEMETIC AGENTS USEFUL THEREIN

[75] Inventors: Jung-Hui Sun, Dublin; Chih-Yun J. Tu, Columbus, both of Ohio

[73] Assignee: Erbamont, Inc., Stamford, Conn.

[21] Appl. No.: 905,215

[22] Filed: Sep. 9, 1986

[51] Int. Cl.⁴ .................. A61K 31/40; A61K 31/445
[52] U.S. Cl. ..................................... 424/10; 546/192; 546/207; 546/209; 546/214; 546/247; 548/240; 548/525; 548/526; 548/567
[58] Field of Search .................. 514/422, 428; 424/10

[56] References Cited

U.S. PATENT DOCUMENTS

| | | | |
|---|---|---|---|
| 3,177,252 | 4/1965 | Thominet et al. | 544/169 X |
| 3,342,826 | 9/1967 | Miller et al. | 260/294 |
| 3,745,175 | 7/1973 | Thominet | 260/326.3 |
| 3,860,619 | 1/1975 | Christensen et al. | 424/285 |
| 4,205,080 | 5/1980 | Carr | 549/60 X |
| 4,207,327 | 6/1980 | Lunsford et al. | 548/356 X |
| 4,536,386 | 8/1985 | Keenan | 424/10 |
| 4,717,563 | 1/1988 | Alphin et al. | 424/10 |
| 4,722,834 | 2/1988 | Teng et al. | 424/10 |

FOREIGN PATENT DOCUMENTS

| | | |
|---|---|---|
| 0068700 | 1/1983 | European Pat. Off. |
| 0095262 | 11/1983 | European Pat. Off. |
| 0099789 | 2/1984 | European Pat. Off. |
| 0124783 | 11/1984 | European Pat. Off. |
| 0158532 | 10/1985 | European Pat. Off. |
| 2325370 | 4/1977 | France |
| 2396757 | 2/1979 | France |
| WO84/00166 | 1/1984 | PCT Int'l Appl. |
| WO84/03281 | 8/1984 | PCT Int'l Appl. |
| 1466822 | 3/1977 | United Kingdom |
| 1481251 | 7/1977 | United Kingdom |
| 2160871A | 1/1986 | United Kingdom |

OTHER PUBLICATIONS

Swann et al., British Medical Journal p. 1188, (1979).

*Primary Examiner*—Joseph Paul Brust
*Attorney, Agent, or Firm*—Smith & Schnacke

[57] ABSTRACT

A method for alleviating emesis caused by chemotherapy which comprises administering an antiemetic agent or a pharmaceutically acceptable salt thereof to a patient in conjunction with the administration of a chemotherapeutic agent, said antiemetic agent being represented by the formula (I)

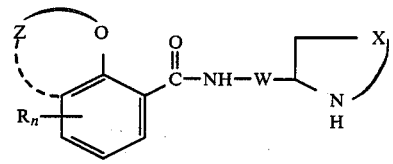

wherein Z represents a substituent such as a lower alkyl group, a methoxyethoxymethyl group, or a benzoylmethyl group; or Z in conjunction with the adjacent position represents the atoms necessary to complete a 5 to 7 membered saturated or unsaturated oxygen-containing ring; R represents a hydrogen atom, a halogen atom, a lower alkyl group, a cycloalkyl group, a lower alkoxy group, an amino group, an alkylsulfonyl group, a lower alkyl-substituted amino group, an acylamido group, a sulfamoyl group, a sulfonamido group or a nitro group; n is an integer of 1 to 3; W is a straight chain or branched chain alkylene group of 1 to 4 carbon atoms; and X represents the atoms necessary to complete a 5 or 6 membered ring; said antiemetic agent being administered in an amount and in a manner which alleviates emesis associated with said chemotherapeutic agent; and certain new antiemetic agents useful in said method.

24 Claims, No Drawings

METHOD FOR CONTROLLING EMESIS CAUSED BY CHEMOTHERAPEUTIC AGENTS AND ANTIEMETIC AGENTS USEFUL THEREIN

BACKGROUND OF THE INVENTION

The present invention relates to a method for alleviating emesis associated with the administration of chemotherapeutic agents.

In cancer chemotherapy, violent emesis often interferes with acceptance of the therapy by the patient. This is particularly true in administering platinum compounds such as cisplatin (cis-dichlorodiamine platinum II) but it is also true in administering other chemotherapeutic agents such as dacarbazine, cyclophosphamide and doxorubicin.

With the exception of metoclopramide, standard antiemetics have been of little value in treating emesis in cancer therapy. U.S. Pat. No. 4,536,386 to Keenan discloses that metoclopramide has been effective in alleviating emesis caused by cisplatin when it is administered in very high dosages beginning prior to cisplatin administration and continuing through post administration.

A critical drawback in administering common antiemetics, including metoclopramide, in treating the emesis associated with chemotherapy is that many benzamide-type antiemetic agents possess dopamine receptor antagonist activity. In pharmacological studies they block both apomorphine stereotypy and emesis. Consequently, certain effects related to blockade of central dopamine receptors, including extrapyramidal side effects, can accompany the administration of these drugs. This makes the drugs less desirable for use in conjunction with chemotherapy in which they are often administered in high dosages over prolonged periods of time. Many patients prefer to suffer emesis instead of the side effects attributed to the antiemetic agent. This is particularly true after one or two days of chemotherapy when emesis is less severe.

SUMMARY OF THE INVENTION

A principal object of the present invention is to provide antiemetic agents which are useful in alleviating emesis caused by chemotherapeutic agents.

A more particular object of the present invention is to provide antiemetic agents which are useful in alleviating emesis associated with the administration of chemotherapeutic agents and which exhibit limited or essentially no dopamine receptor antagonist activity.

These and other objects are accomplished in accordance with the present invention which provides:

A method for alleviating emesis associated with chemotherapy which comprises:

administering an antiemetic agent or a pharmaceutically acceptable salt thereof to a patient in conjunction with the administration of a chemotherapeutic agent, said antiemetic agent being a compound of the formula (I):

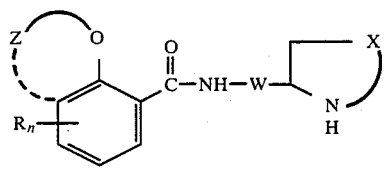

wherein Z represents a lower alkyl group or Z in conjunction with the adjacent position represents the carbon and hydrogen atoms necessary to complete a 5 to 7 membered saturated or unsaturated ring; R represents a hydrogen atom, a lower alkyl group, a cycloalkyl group, a lower alkoxy group, an amino group, an alkylsulfonyl group, a lower alkyl substituted amino group, an acylamido group, a sulfamoyl group, a sulfonamido group, a halogen atom, or a nitro group; W is a straight chain or branched chain alkylene group of 1 to 4 carbon atoms; X represents the carbon and hydrogen atoms necessary to complete a 5 or 6 membered ring; and n is an integer of 1 to 3 provided when n is 2 or 3 R may be the same or different; or a pharmaceutically acceptable salt thereof.

In formula (I), Z is more particularly

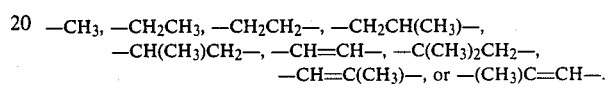

In accordance with one embodiment of the present invention, the antiemetic agent is represented by the formula (II)

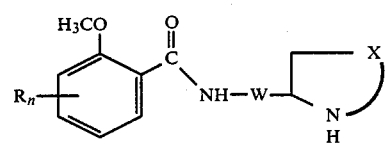

where W, R, X and n are defined as above.

In accordance with the preferred embodiments of the present invention, in formulas (I) and (II) above X represents the atoms necessary to complete a pyrrolidinyl ring and W is a methylene group. Still more preferably, n is 1 and R is 5-amino, 4-methylamino, or 5-chloro; or n is 2 and the R groups are a combination of a 4-amino and a 5-chloro group.

In accordance with another embodiment of the invention, the antiemetic agent is represented by the formulas (III) or (IV) and more particularly by the formulas (IIIa) or (IVa).

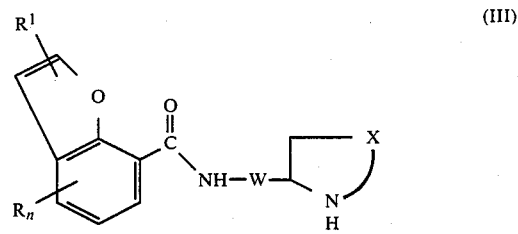

(III)

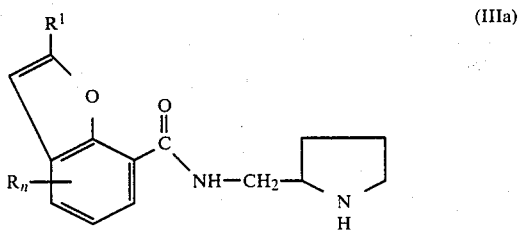

(IIIa)

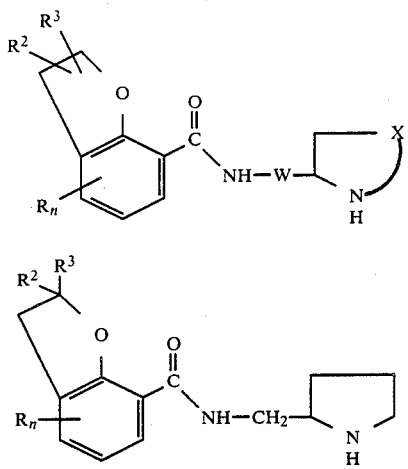

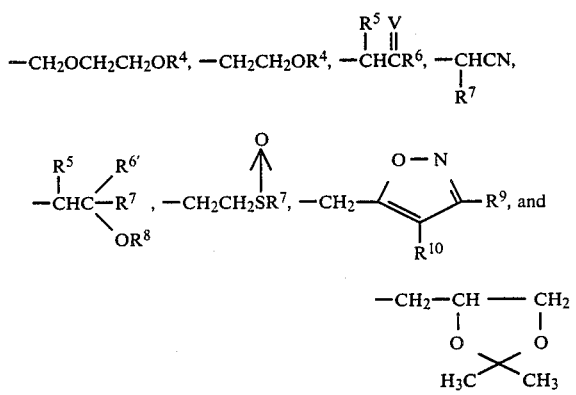

where W, X, R and n are defined as in formula I and $R^1$, $R^2$ and $R^3$ may be the same or different and are selected from the group consisting of a hydrogen atom, an alkyl group having 1 to 3 carbon atoms, or a phenyl group.

In accordance with another embodiment of the invention Z in formula (I), is selected from the group consisting of:

$$-CH_2OCH_2CH_2OR^4, -CH_2CH_2OR^4, \overset{R^5}{\underset{|}{-CHCR^6}}\overset{V}{\underset{|}{\|}}, -\underset{|}{\overset{}{CHCN}},$$
$$R^7$$

$$\overset{R^5}{\underset{|}{-CHC}}\overset{R^{6'}}{\underset{\diagdown}{\diagup}}R^7, -CH_2CH_2SR^7, -CH_2-\underset{R^{10}}{\overset{O-N}{\diagup\diagdown}}R^9, \text{ and}$$
$$OR^8$$

$$-CH_2-\underset{|}{CH}\underset{|}{\quad}CH_2$$
$$\underset{H_3C}{\overset{O}{\diagdown}}\underset{CH_3}{\overset{O}{\diagup}}$$

where V is oxygen or $NOR^{11}$, $R^7$ is hydrogen or (lower)alkyl; $R^4$, $R^5$, $R^8$ and $R^{11}$ are the same or different, and are hydrogen, (lower)alkyl, (lower)alkenyl, (lower)alkynyl, (lower)alkoxy(lower)alkyl or cycloalkyl provided that, when $R^4$, $R^8$ or $R^{11}$ is (lower)alkenyl or (lower)alkynyl, the unsaturated carbon atom may not be directly attached to an oxygen atom; $R^6$ is hydrogen, halogen, (lower)alkyl, (lower)alkoxy, hydroxy, hydrazino, (lower)alkoxycarbonyl(lower)alkenyl, acetylhydrazino, thienyl, phenyl, phenyl(lower)alkyl or $NR^4R^5$; $R^9$ and $R^{10}$ are the same or different and are hydrogen or methyl; or $R^5$ and $R^6$, taken together with the carbon atoms to which they are attached may form a saturated or unsaturated ring of from 5 to 7 atoms, inclusive, optionally containing at least one heteroatom selected from oxygen, sulfur and nitrogen; or $R^{6'}$ and $R^8$, taken together with the carbon and oxygen atoms to which they are attached, may form a 3 to 6 membered saturated oxygen-containing ring, $R^{6'}$ has the same definition as $R^6$ except it is not halogen or hydroxy; or nontoxic pharmaceutically acceptable salts, hydrates, solvates or quaternary ammonium salts thereof.

Representative examples of Z are: 2-hydroxyethyl; 2,2-dimethoxyethyl; 2-methoxyethyl; 2-propanon-1-yl; benzoylmethyl; butan-2-on-3-yl; cyclohexanon-2-yl; 5-hexen-2-on-3-yl; (2-hydroxyimino)propan-1-yl; (2-methoxyimino)propan-1-yl; 2-hydroxypropan-1-yl; cyanomethyl; carboxamidomethyl; 2-butyn-1-yl; 2-(methylsulfinyl)ethyl; pentan-2-on-3-yl; 2-butanon-1-yl; pentan-2-on-1-yl; pentan-3-on-2-yl; 2-hydrazino-2-oxoethyl; 2-hydroxybutan-3-yl; 2-(methylamino)-2-oxoethyl; ethyl 3-methoxycroton-4-yl; 1,3-dioxolan-2-yl; oxazolidin-2-on-5-ylmethyl; 2-pyridinomethyl; tetrahydrofurfuryl; and 2-methoxyethoxyethyl. Of these 2-methoxyethoxymethyl; benzoylmethyl; cyclohexanon-2-yl; (2-hydroxyimino)propan-1-yl; and 3-phenyl-2-propanon-1-yl are particularly preferred.

It has been found that the antiemetic agents administered in accordance with the present invention alleviate the emesis associated with the administration of chemotherapeutic agents and yet exhibit little or no dopamine receptor blocking activity. Thus, these compounds can be used in conjunction with chemotherapy to alleviate emesis without the undesirable side effects which accompany the administration of other antiemetics. Applicants' discovery is surprising since it is believed that emesis and psychosis are controlled by similar dopamine receptors in the brain. Previously it was believed that benzamides which did not exhibit dopamine receptor antagonist activity would not be functional in controlling emesis. While it is not entirely clear how chemotherapeutically induced emesis is controlled in the present invention, one theory is that it relates to blocking receptors in the chemoreceptor tripper zone (CTZ).

In accordance with the invention, the antiemetic agents are administered in amounts sufficient to alleviate emesis. The exact dosage will vary depending upon the antiemetic agent and the chemotherapeutic agent used. Usually the compounds will be administered intravenously in amounts ranging from about 0.01 to 20 mg per kg patient body weight. The administration frequency and schedule will vary. Typically the antiemetic agent is administered beginning prior to the administration of the chemotherapeutic agent and continuing into the postadministration period. The agent can be administered continuously or periodically.

The method of the present invention is useful in alleviating emesis associated with the administration of chemotherapeutic agents and, particularly, the platinum compound cisplatin, dacarbazine, cyclophosphamide, 5-fluorouracil and doxorubicin.

DEFINITIONS

The term "lower" as it occurs in the terms "lower alkyl", "lower alkoxy", etc. refers to groups containing 1 to 6 carbon atoms.

The term "cycloalkyl" includes cycloalkyl groups containing 4 to 8 carbon atoms.

The terms "acylamido" and "sulfonamido" more specifically include moieties of the formulae $-NHCOR^{12}$ and $-NHSO_2R$ where R is a lower alkyl group.

The term "halogen atom" includes fluorine, chlorine, bromine and iodine atoms.

The term "pharmaceutically acceptable salts" includes but is not limited to hydrochlorides, phosphates, fumarates, citrates, tartarates, etc.

DETAILED DESCRIPTION OF THE INVENTION

Many of the antiemetic agents used in the present invention are known or they can be synthesized in a known manner. In particular, many of the antiemetic agents used in the present invention are prepared by reacting the appropriately substituted benzoic acid, benzofurancarboxylic acid, dihydrobenzofurancarboxylic acid, or esters or the acid chloride thereof with a amine of the formula (V)

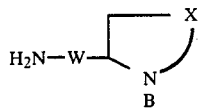

where W and X are defined as above and B is a readily hydrolyzable nitrogen protecting group. More particularly, the amine is a protected 2-aminomethylpyrrolidine of the formula (Va).

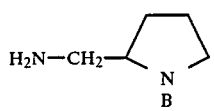

After reacting with the acid, ester or acid chloride, the protecting group is removed. Representative examples of protecting groups include a trityl group, a benzyl group or p-methoxybenzyl group.

The amine can be prepared from proline by the process described in Florvall, L. et al., *J. Med. Chem.* 1982, 25, 1280–86, 1982, as follows:

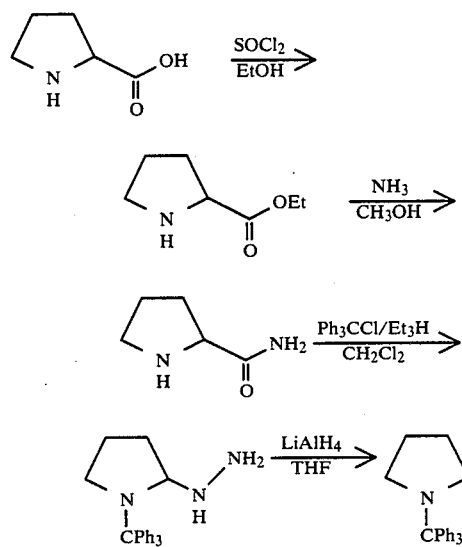

The unprotected amine can also be prepared by the process described in U.K. Pat. No. 1,481,251. That process comprises reacting 2-pyrrolidone with a reactive benzylated compound having the formula Y—CH$_2$-C$_6$H$_5$, in which Y represents a reactive group or atom, in a basic medium in the presence of a solvent to produce N-benzyl-2-pyrrolidone, and treating that compound with a dialkylsulphate and an alkali metal alkoxide, followed by nitromethane, to produce N-benzyl-2-nitromethylenepyrrolidine. The latter is either (a) reduced to 2-aminomethylpyrrolidine by hydrogen in the presence of a catalyst either directly or through the intermediate N-benzyl-2-aminomethylpyrrolidine or (b) reduced to N-benzyl-2-aminomethylpyrrolidine by a metal system (e.g., Raney nickel) and then to 2-aminomethylpyrrolidine by hydrogen in the presence of a metal catalyst and an acid (e.g., Raney nickel and HCl). The 2-aminomethylpyrrolidine is then optionally converted to an acid-addition salt by treatment with an acid, which may be mineral or organic.

Carboxylic acids useful in preparing the antiemetic agents used in the present invention can be prepared by known methods or are commercially available.

Benzofurancarboxylic acids, dihydrobenzofurancarboxylic acids, and benzopyrancarboxylic acids useful in preparing the antiemetic agents used in the present invention can be prepared by the processes described in commonly assigned U.S. application Ser. No. 564,641, now abandoned, filed Dec. 22, 1983.

An alternative method of preparing the compounds utilizes an appropriately substituted carboxylic acid which is reacted with ethyl chloroformate to form a mixed anhydride of the acid which is subsequently reacted with a solution of the protected amine (e.g., in dichloromethane). This method simplifies the synthesis where the carboxylic acid includes one or more substituents, such as an amino group, which is capable of reacting with the carboxyl group in competition with the amine. For further explanation of the alternative synthesis see U.S. Pat. No. 4,207,327.

U.K. Pat. No. 1,466,822 discloses a further synthesis in which the amine is reacted directly with the ester or acid chloride of the acid.

When Z is a moiety selected from

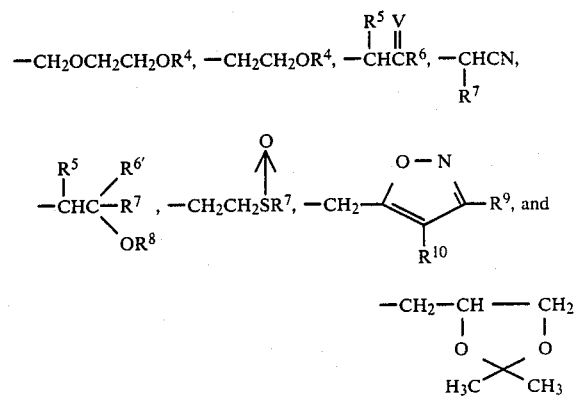

where V and R$^4$–R$^{10}$ are defined as above, the compounds can be prepared by the procedures outlined in Great Britain patent application No. 2160871A of Jan. 2, 1986. Depending on the structure of the compound, it may be prepared by a simple substitution reaction in which the corresponding 2-hydroxybenzamide is reacted with a compound of the formula Z-L where L is a leaving group. In other cases, a benzoic acid or ester having the appropriate 2-substitution may be reacted with an amine as described above. Other procedures as outlined in the aforementioned published application may also be used.

Representative examples of antiemetic agents particularly useful in the present invention include the following:

5-chloro-N-(2-pyrrolidinylmethyl)-2,3-dihydrobenzo[b]furan-7-carboxamide 5-amino-N-(2-pyrrolidinylmethyl)-2,3-dihydrobenzo[b]furan-7-carboxamide 4-amino-5-chloro-N-(2-pyrrolidinylmethyl)-2,3-dihydrobenzo[b]furan-7-carboxamide 4-amino-5-chloro-2-methoxy-N-(2-pyrrolidinylmethyl)-benzamide 6-chloro-N-(2-piperidinylmethyl)-2,3-dihydrobenzo[b]furan-7-carboxamide Many of the antiemetic agents used herein have an asymmetric carbon atom and exist as a D- or L-isomer. These compounds can be used as the racemate or as the D- or L-isomer. A tendency for the L-isomer to be more active than the racemate has been noted in early studies.

The present invention is illustrated in more detail by the following biological examples wherein the following compounds 1-4 and comparison compounds C1-C4 were used.

| Compound No. | Name |
|---|---|
| 1. | (L)-5-chloro-N—(2-pyrrolidinylmethyl)-2,3-dihydrobenzo[b]furan-7-carboxamide hydrochloride |
| 2. | (L)-5-amino-N—(2-pyrrolidinylmethyl)-2,3-dihydrobenzo[b]furan-7-carboxamide hydrochloride |
| 3. | (L)-4-amino-5-chloro-N—(2-pyrrolidinylmethyl)-2,3-dihydrobenzo[b]furan-7-carboxamide hydrochloride |
| 4. | (L)-4-amino-5-chloro-2-methoxy-N—(2-pyrrolidinylmethyl)benzamide hydrochloride |
| C-1. | 5-chloro-N—(1-ethyl-2-pyrrolidinylmethyl)-2,3-dihydrobenzo[b]furan-7-carboxamide hydrochloride |
| C-2. | 5-amino-N—(1-ethyl-2-pyrrolidinylmethyl)-2,3-dihydrobenzo[b]furan-7-carboxamide hydrochloride |
| C-3. | 4-amino-5-chloro-N—(1-ethyl-2-pyrrolidinylmethyl)-2,3-dihydrobenzo[b]furan-7-carboxamide fumarate |
| C-4. | 4-amino-5-chloro-2-methoxy-N—(1-ethyl-2-pyrrolidinylmethyl)benzamide |

EXAMPLE 1

Dopamine Turnover

Male Sprague Dawley rats were injected intravenously with various doses of test compound and whole brain was removed at a predetermined time after dosing. The striatum was dissected from the brain, homogenized in a buffer/organic solvent mixture, clarified with a centrifuge, and an aliquot of the supernatant analyzed for 3,4-dihydroxyphenylacetic acid (DOPAC) by high performance liquid chromatography coupled with an electrochemical detector. The results of the studies are given in Table 1. The results are expressed as the percent change from control. The standard deviation of the data generally required a difference of 18% from control to be statistically significant at the 0.05 level as determined by the Student's "t" test. DOPAC is a metabolite of dopamine. A high concentration of DOPAC in the striatum relative to the control indicates that the drug is a dopamine antagonist.

TABLE 1

The Response of Striatal DOPAC to Various Concentrations of Test Compound

| Compound | Dosage mg/kg | | | | | |
|---|---|---|---|---|---|---|
| | 0.1 | 0.3 | 1.0 | 3.3 | 10 | 33 |
| Metoclopramide | 1.2 | 12.4 | 81.2 | 192.0 | 384.6 | — |
| 1 | — | −11.6 | −0.6 | −2.5 | 91.8 | 255.4 |
| 2 | — | 0.0 | −6.5 | −17.3 | 0.0 | −10.7 |
| 3 | — | −14.4 | −10.0 | −6.2 | −2.7 | 6.4 |
| 4 | — | −1.9 | −3.3 | −3.7 | 13.7 | 41.6 |

The data in Table 1 suggest that metoclopramide exhibits strong dopamine antagonism at doses of 1.0 mg/kg and greater whereas the compounds used in the present invention do not exhibit such activity except at exceedingly high dosages.

EXAMPLE 2

Compounds 1-4 and C-1 to C-4 and metoclopramide were examined in the cisplatin emesis, apomorphine climbing and catalepsy protocols summarized below. The results are reported in Table 2.

Cisplatin Emesis

Mature Beagle dogs of either sex, weighing 7-16 kg, were individually caged with water available ad libitum. Each animal was offered 300 g of Purina Dog Chow the day of an experiment. Drug in varying doses or carrier was administered intravenously 30 minutes before and 120 minutes after intravenous bolus administration of 3 mg/kg cisplatin (Ben Venue Laboratories, Inc., Bedford, Ohio). In all experiments the animals were observed for five hours post cisplatin administration and each emetic event (i.e., expulsion of material) was recorded. Emesis was considered blocked if the animal suffered 2 or less emetic events. Based upon these observations, $ED_{50}$ values were determined for each of the compounds tested.

Apomorphine Climbing

Male ICR-Swiss mice (Harlan Industries, Indianapolis, Ind.), weighing 25-29 g, were placed in $8 \times 10 \times 16$ cm wire cages. After a 1 to 1.5 hour acclimatization period, drug or carrier was administered intraperitoneally. Apomorphine hydrochloride (Lilly; 1 mg/kg) or carrier (saline, 10.0 ml/kg) was administered subcutaneously 30 minutes after test compound administration. Climbing behavior was assessed 20 minutes after apomorphine injection using the following scoring system:

(0) 4 paws on the floor of the cage
(1) 1, 2, or 3 paws grasping a side of the cage
(2) 4 paws grasping a side of the cage.

Climbing indexes were calculated using the formula:

$$\text{Climbing Index} = \frac{\text{sum of individual scores} \times \% \text{ of animals graded 1 or 2}}{\text{number of animals}}$$

50% ED values (i.e., the dose of drug which yields a climbing index of 100) were calculated using regression equations.

Catalepsy

Female Sprague Dawley rats (Harlen Industries, Indianapolis, Ind.), weighing 160-225 g, were used. The animals (n=6) were injected intravenously with drug (20 mg/kg) or carrier (saline; 2 ml/kg) and were tested one and two hours later. This involved placing the front paws of the rat on a horizontal metal bar suspended 10 cm above the table top and recording the number of seconds, to a maximum of 60, that the animal remains in this position. Each animal was tested three times in succession and the average time the animal remained on the bar was calculated. Student's non-paired "t" test was employed to determine the significance of differences between the control and treated groups. If the time the treated animals remained on the bar was significantly longer than the control animals, catalepsy is indicated.

TABLE 2

| Compound | Cisplatin Emesis ED$_{50}$ (mg/kg. i.v.) | Apomorphine Climbing 50% ED (mg/kg i.p.) | Catalepsy (20 mg/kg i.v.) |
|---|---|---|---|
| 1 | 0.6 | 36.2 | No |
| 2 | ca. 1.75 | 100 | No |
| 3 | ca. 0.42 | 75 | No |
| 4 | 1.0 | 44.5 | No |
| Metoclopramide | 1.1 | 1.7 | Yes |
| C-1 | 1.0 | 0.91 | Yes |
| C-2 | 2.5 | 10.4 | No |
| C-3 | 0.7 | 1.5 | Yes |
| C-4 | 1.0 | 0.44 | Yes |

The data in Table 2 indicate that Compounds 1–4 are potent Cisplatin antiemetics but weak dopamine antagonists (Note the high 50% ED values in apomorphine climbing and the absence of catalepsy). By contrast, the comparison compounds, C-1 to C-4, which differ from Compounds 1–4 only in the inclusion of an ethyl group on the pyrrolidine ring and metoclopramide are effective antiemetics but also strong dopamine antagonists.

EXAMPLE 3

Compounds 1–4 and metoclopramide were tested as follows.

Dacarbazine Emesis

Mature beagle dogs (7–16 kg) were used in these experiments. The animals were individually caged with water available ad libitum. Each dog was offered 300 g of Purina Dog Chow the day of an experiment. Drug (mg base/kg) or carrier (0.9% saline; 0.2 ml/kg) was administered intravenously 30 minutes before and 120 minutes after intravenous bolus administration of 10 mg/kg dacarbazine (10 mg DTIC/ml saline; Miles Pharmaceuticals). The animals were observed for 5 hours post dacarbazine administration. If the animal suffered 2 or less emetic events, the animal was considered protected.

Apomorphine Emesis

Mature beagle dogs, individually caged and weighing 10.6–14.5 kg, were used in these experiments. The animals were fed just before being dosed intravenously with drug (mg base/kg) or carrier (0.9% saline; 0.2 ml/kg). Each animal received 0.1 mg/kg apomorphine hydrochloride (1 mg/ml saline; Lilly) subcutaneously thirty minutes after administration of the test compound. The animals were observed for 1 hour post apomorphine administration. If the animal had no emetic events, the animal was considered protected.

TABLE 3

Dacarbazine-induced Emesis In The Dog

| Treatment | Dose (mg/kg IV × 2) | Number Protected/Number Dosed |
|---|---|---|
| Saline | — | 1/4 |
| Metoclopramide | 1.0 | 3/4 |
| Compound 1 | 1.0 | 4/4 |
| Compound 2 | 1.0 | 4/4 |
| Compound 3 | 1.0 | 4/4 |

TABLE 4

Apomorphine-induced Emesis In The Dog

| Treatment | Dose (mg/kg IV) | Number Protected/Number Dosed |
|---|---|---|
| Saline | — | 0/6 |
| Metoclopramide | 0.125 | 2/4 |
|  | 1.0 | 4/4 |
| Compound 1 | 1.0 | 0/2 |
|  | 2.0 | 2/2 |
| Compound 2 | 4.0 | 0/4 |
| Compound 3 | 1.0 | 0/4 |
|  | 2.0 | 0/4 |
|  | 4.0 | 0/4 |
| Compound 4 | 1.0 | 0/4 |

Having described the invention in detail and by reference to the preferred embodiments thereof, numerous modifications and variations are possible without departing from the scope of the following claims.

What is claimed is:

1. A method for alleviating emesis caused by chemotherapy in cancer chemotherapy which comprises administering an antiemetic agent or a pharmaceutically acceptable salt thereof to a patient in conjunction with the administration of a chemotherapeutic agent, said antiemetic agent being represented by the formula (I)

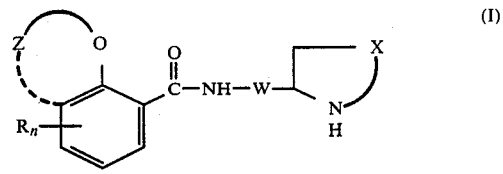

(I)

wherein Z represents a lower alkyl group or Z in conjunction with the adjacent position represents the carbon and hydrogen atoms necessary to complete a 5 to 7 membered saturated or unsaturated oxygen-containing ring; R represents a hydrogen atom, a halogen atom, a lower alkyl group having 1 to 6 carbon atoms, a cycloalkyl group having 4 to 8 carbon atoms, a lower alkoxy group having 1 to 6 carbon atoms, an amino group, a lower alkyl-substituted amino group wherein the alkyl group has 1 to 6 carbon atoms, an acylamido group of the formula —NHCOR$^{12}$ where R$^{12}$ is an alkyl group containing 1 to 6 carbon atoms, a sulfamoyl group, a sulfonamido group of the formula —NHSO$_2$R$^{12}$ where R$^{12}$ is defined as above or a nitro group; n is an integer of 1 to 3; W is a straight chain or branched chain alkylene group of 1 to 4 carbon atoms; and X represents the carbon and hydrogen atoms necessary to complete a 5 or 6 membered ring; said antiemetic agent being administered in an amount and in a manner which alleviates emesis associated with said chemotherapeutic agent.

2. The method of claim 1 wherein said chemotherapeutic agent is selected from the group consisting of cisplatin, dacarbazine, cyclophosphamide and doxorubicin.

3. The method of claim 2 wherein said antiemetic agent is represented by the formula II

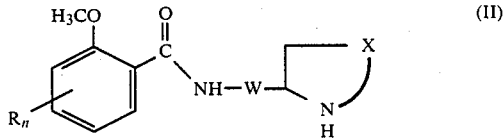

(II)

where R, W, X, and n are defined as in claim 1.

4. The method of claim 3 wherein W is a methylene group and X represents the atoms necessary to complete a pyrrolidinyl ring.

5. The method of claim 4 wherein R is a chlorine atom, a bromine atom, an amino group, a lower alkyl-substituted amino group or a methoxy group.

6. The method of claim 1 wherein said antiemetic agent is represented by the formula III

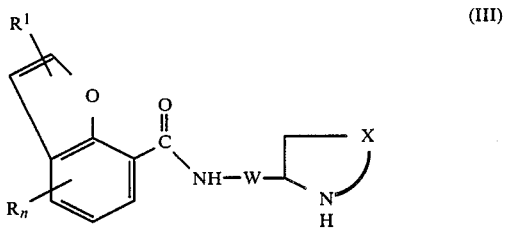

where $R^1$ represents a hydrogen atom, a lower alkyl group, or a phenyl group and W, R, X, and n are defined as in claim 1.

7. The method of claim 6 wherein W is a methylene group and X represents the atoms necessary to complete a pyrrolidinyl ring.

8. The method of claim 7 wherein R is a chlorine atom, a bromine atom, an amino group, a lower alkyl-substituted amino group or a methoxy group.

9. The method of claim 1 wherein said antiemetic agent is represented by the formula (IV)

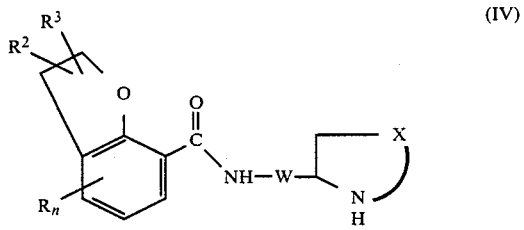

where $R^2$ and $R^3$ may be the same or different and represent a hydrogen atom, a lower alkyl group, or a phenyl group and W, R, X, and n are defined as in claim 1.

10. The method of claim 9 wherein W is a methylene group and X represents the atoms necessary to complete a pyrrolidinyl ring.

11. The method of claim 10 wherein R is a chlorine atom, a bromine atom, an amino group, a lower alkyl-substituted amino group or a methoxy group.

12. The method of claim 8 wherein $R^1$ is a hydrogen atom.

13. The method of claim 11 wherein $R^2$ and $R^3$ are hydrogen atoms.

14. The method of claim 8 wherein R is selected from the group consisting of a chlorine atom and an amino group.

15. The method of claim 11 wherein R is selected from the group consisting of a chlorine atom and an amino group.

16. The method of claim 1 wherein said antiemetic agent is 5-chloro-N-(2-pyrrolidinylmethyl)-2,3-dihydrobenzo[b]furan-7-carboxamide or a salt pharmaceutically acceptable thereof.

17. The method of claim 1 wherein said antiemetic agent is 5-amino-N-(2-pyrrolidinylmethyl)-2,3-dihydrobenzo[b]furan-7-carboxamide or a salt pharmaceutically acceptable thereof.

18. The method of claim 1 wherein said antiemetic agent is 4-amino-5-chloro-N-(2-pyrrolidinylmethyl)-2,3-dihydrobenzo[b]furan-7-carboxamide or a salt pharmaceutically acceptable thereof.

19. The method of claim 1 wherein said antiemetic agent is 4-amino-5-chloro-2-methoxy-N-(2-pyrrolidinylmethyl)benzamide or a salt pharmaceutically acceptable thereof.

20. The method of claim 1 wherein said antiemetic agent is 4-methylamino-5-chloro-N-(2-pyrrolidinylmethyl)-2,3-dihydrobenzo[b]furan-7-carboxamide or a salt pharmaceutically acceptable thereof.

21. The method of claim 1 wherein said antiemetic agent is 6-chloro-N-(2-pyrrolidinylmethyl)dihydrobenzo[b]pyran-8-carboxamide or a salt pharmaceutically acceptable thereof.

22. The method of claim 1 wherein said antiemetic agent is 5-chloro-N-(2-piperidinylmethy)-2,3,-dihydrobenzo[b]furan-7-carboxamide.

23. The method of claim 1 wherein, when said antiemetic agent exists as an optical isomer, said antiemetic agent is the L-isomer.

24. The method of claim 6 wherein W is a methylene group and X represents the atoms necessary to complete a pyrrolidinyl ring.

* * * * *